United States Patent
Weitekamp et al.

(10) Patent No.: US 9,573,125 B2
(45) Date of Patent: Feb. 21, 2017

(54) FUNCTIONAL N-HETEROCYCLES FOR SOLID-SUPPORTED CATALYSIS

(71) Applicant: California Institute of Technology, Pasadena, CA (US)

(72) Inventors: Raymond Weitekamp, Glendale, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 60 days.

(21) Appl. No.: 13/928,155

(22) Filed: Jun. 26, 2013

(65) Prior Publication Data

US 2014/0005036 A1  Jan. 2, 2014

Related U.S. Application Data

(60) Provisional application No. 61/664,571, filed on Jun. 26, 2012.

(51) Int. Cl.

| | | |
|---|---|---|
| B01J 31/22 | (2006.01) | |
| C08F 4/44 | (2006.01) | |
| C07D 233/02 | (2006.01) | |
| B01J 31/16 | (2006.01) | |
| C07F 9/6506 | (2006.01) | |
| B01J 31/02 | (2006.01) | |

(52) U.S. Cl.
CPC ............. *B01J 31/22* (2013.01); *B01J 31/1625* (2013.01); *B01J 31/2273* (2013.01); *C07F 9/65062* (2013.01); *B01J 31/0259* (2013.01); *B01J 2231/543* (2013.01); *B01J 2531/17* (2013.01); *B01J 2531/18* (2013.01); *B01J 2531/821* (2013.01); *B01J 2540/64* (2013.01); *Y02P 20/582* (2015.11)

(58) Field of Classification Search
None
See application file for complete search history.

(56) References Cited

U.S. PATENT DOCUMENTS

2003/0083445 A1 * 5/2003 Grubbs .................. C08G 61/06
526/161

OTHER PUBLICATIONS

Mayr et al. Adv. Synth. Catal. 2002, 344, 712-719.*
Jordan et al. Angew. Chem. Int. Ed, 2007, 46, 5152-5155.*
W.A. Herrmann. "N-Heterocyclic Carbenes: A New Concept in Organometallic Catalysis." *Angew. Chem. Int. Ed.*, 2002, 41, 1290-1309.
K.M. Kuhn et al. "A Facile Preparation of Imidazolinium Chlorides." *Org. Lett.*, 2008, 10, 2075-2077.

* cited by examiner

*Primary Examiner* — Yun Qian
(74) *Attorney, Agent, or Firm* — Foley Hoag LLP

(57) ABSTRACT

An efficient method for the preparation of backbone-substituted imidazolinium salts for use as N-heterocyclic carbene ligands, e.g., for organometallic catalysts is provided. These functionalized N-heterocyclic carbene ligands are used to prepare solid-supported catalysts, e.g., for olefin metathesis.

16 Claims, No Drawings

FUNCTIONAL N-HETEROCYCLES FOR SOLID-SUPPORTED CATALYSIS

CROSS-REFERENCE TO RELATED APPLICATIONS

The present application claims the benefit of U.S. Provisional Application No. 61/664,571 filed on Jun. 26, 2012, which is incorporated herein by reference in its entirety.

STATEMENT REGARDING FEDERALLY SPONSORED RESEARCH OR DEVELOPMENT

This research was conducted with Government support under and awarded by Department of Defense (DoD), Air Force Office of Scientific Research, National Defense Science and Engineering Graduate (NDSEG) Fellowship, 32 CFR 168a.

BACKGROUND OF THE INVENTION

Olefin metathesis has gained a prominent place in the chemist's arsenal as a powerful tool for carbon-carbon bond formation due to the development of highly active and versatile catalysts (Handbook of Metathesis; Grubbs, R. H., Ed.; Wiley-VCH). The efficiency and usefulness of these catalysts depend on various factors among which the nature of the ligands present in the catalyst.

Owing to their electronic properties, N-heterocyclic carbenes (NHC) have contributed to the increased stability and reactivity of catalysts, particularly in ruthenium-based olefin metathesis (Scholl et al., Tetrahedron Letters 1999, 40, 2247; Scholl et al., Organic Letters 1999, 1, 953-956; Huang et al., J. Amer. Chem. Soc., 1999, 121, 2674-2678).

Solid-support reagents have been used in chemical syntheses and present many advantages among which the ease of removal/purification from reactions, the safer handling of dangerous or toxic chemicals and the recycling of recovered reagents. For instance, solid-supported catalysts provide an effective strategy to eliminate metal contamination of the metathesis products. However, the preparation of solid-supported catalysts for metathesis can be challenging and result in a catalyst with lower reactivity.

Thus, there is a need for solid-supported catalysts with good reactivity for olefin metathesis and an efficient method for their preparation.

SUMMARY OF THE INVENTION

In one aspect, the invention provides a compound of Formula (I):

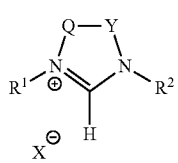

Formula (I)

wherein:
$R^1$ and $R^2$ are independently selected from substituted or unsubstituted alkyl, substituted or unsubstituted aryl, substituted or unsubstituted heteroaryl, substituted or unsubstituted cycloalkyl, carbonyl or sulfonyl;
Q is selected from $CR^3R^4$, $NR^3$, S, SO, or $SO_2$;
Y is selected from $CR^5R^6$, $NR^5$, S, SO, or $SO_2$, preferably selected such that Q and Y are not both $NR^3$ and $NR^5$;
$R^3$, $R^4$, $R^5$ and $R^6$ are independently selected from H, substituted or unsubstituted alkyl, substituted or unsubstituted aryl, substituted or unsubstituted heteroaryl, such that at least one of $R^3$, $R^4$, $R^5$, and $R^6$ comprises a functional group capable of attaching to a functional group on a solid support; and
$X^-$ is a negatively charged counterion.

In certain embodiments, the compound has the structure of Formula (II):

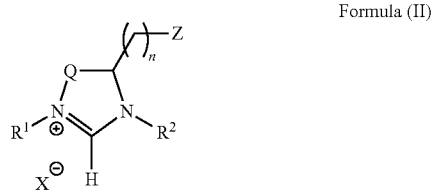

Formula (II)

wherein:
$R^1$ and $R^2$ are independently selected from H, substituted or unsubstituted alkyl, substituted or unsubstituted aryl, or substituted or unsubstituted heteroaryl;
Z is selected from ester, amino, hydroxyl, isocyanate, halogen, sulfate, sulfonic acid, phosphate, phosphonate, phosphonic acid or carboxy, or a salt thereof; and
n is an integer from 1-20, preferably from 1-6, such as 1, 2 or 3.

In one aspect, the invention provides a compound of Formula (III):

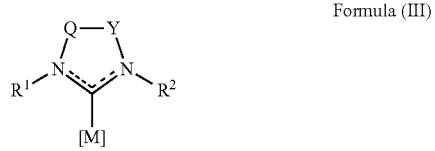

Formula (III)

wherein:
$R^1$ and $R^2$ are independently selected from substituted or unsubstituted alkyl, substituted or unsubstituted aryl, substituted or unsubstituted heteroaryl, substituted or unsubstituted cycloalkyl, carbonyl or sulfonyl;
Q is selected from $CR^3R^4$, $NR^3$, S, SO, or $SO_2$;
Y is selected from $CR^5R^6$, $NR^5$, S, SO, or $SO_2$, preferably selected such that Q and Y are not both $NR^3$ and $NR^5$;
$R^3$, $R^4$, $R^5$ and $R^6$ are independently selected from H, substituted or unsubstituted alkyl, substituted or unsubstituted aryl, substituted or unsubstituted heteroaryl, such that at least one of $R^3$, $R^4$, $R^5$, and $R^6$ comprises a functional group capable of attaching to a functional group on a solid support; and
[M] is a transition metal complex.

In certain embodiments, the compound has the structure of Formula (IV)

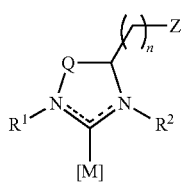

Formula (IV)

wherein:
R¹ and R² are independently selected from H, substituted or unsubstituted alkyl, substituted or unsubstituted aryl, or substituted or unsubstituted heteroaryl;
Z is selected from ester, amino, hydroxyl, isocyanate, halogen, sulfate, sulfonic acid, phosphate, phosphonate, phosphonic acid or carboxy or a salt thereof;
n is an integer from 1-20, preferably from 1-6, such as 1, 2 or 3; and
[M] is a transition metal complex.

In certain embodiments, Z is selected from organosilane, ester, amino, hydroxyl, isocyanate, halogen, sulfate, sulfonic acid, phosphate, phosphonate, phosphonic acid or carboxy or a salt thereof.

In certain preferred embodiments, Z is selected from phosphonate, phosphonic acid, or a semi-ester thereof.

In certain preferred embodiments, n is 1.

In certain embodiments, R¹ and R² are independently substituted or unsubstituted aryl.

In certain preferred embodiments, R¹ and R² are mesityl.

In certain preferred embodiments, Q is CR³CR⁴.

In certain preferred embodiments, R³ and R⁴ are both H.

In certain preferred embodiments, the compound has the structure of Formula (V):

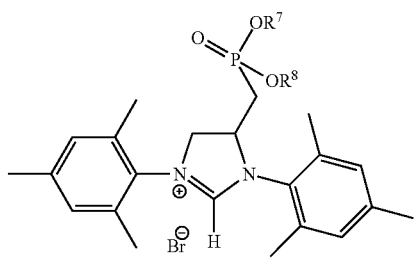

Formula (V)

wherein R⁷ and R⁸ are independently H or alkyl or a salt thereof.

In certain preferred embodiments, the compound has the structure of Formula (VI):

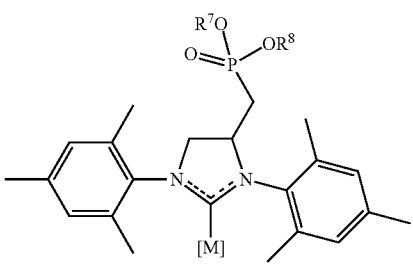

Formula (VI)

wherein R⁷ and R⁸ are independently H or alkyl or a salt thereof.

In certain preferred embodiments, R⁷ and R⁸ are lower alkyl.

In certain embodiments, R¹, R² or Z is a solubilizing group.

In one aspect, the invention provides a method for preparing a compound of Formula (I),

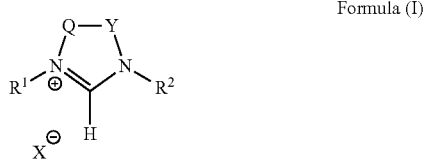

Formula (I)

wherein:
R¹ and R² are independently selected from substituted or unsubstituted alkyl, substituted or unsubstituted aryl, substituted or unsubstituted heteroaryl, substituted or unsubstituted cycloalkyl, carbonyl or sulfonyl;
Q is selected from CR³R⁴, NR³, S, SO, or SO₂;
Y is selected from CR⁵R⁶, NR³, S, SO or SO₂, preferably selected such that Q and Y are not both NR³ and NR⁵;
R³, R⁴, R⁵ and R⁶ are independently selected from H, substituted or unsubstituted alkyl, substituted or unsubstituted aryl, substituted or unsubstituted heteroaryl, such that at least one of R³, R⁴, R⁵, and R⁶ comprises a functional group capable of attaching to a functional group on a solid support; and
X⁻ is a negatively charged counterion;
wherein the method comprises reacting the compound of Formula (VII) with a compound of Formula (VIII) in the presence of a base

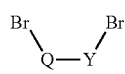

Formula (VII)

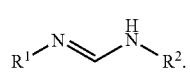

Formula (VIII)

In certain embodiments, the method comprises reacting a compound of Formula (IX)

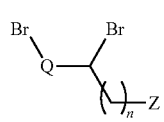

Formula (IX)

with the compound of Formula (VIII) in the presence of a base to prepare a compound of Formula (II)

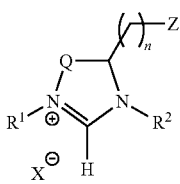

Formula (II)

wherein:
R¹ and R² are independently selected from H, substituted or unsubstituted alkyl, substituted or unsubstituted aryl, or substituted or unsubstituted heteroaryl;
Z is selected from organosilane, ester, amino, hydroxyl, isocyanate, halogen, sulfate, sulfonic acid, phosphate, phosphonate, phosphonic acid or carboxy (preferably from organosilane, ester, amino, hydroxyl, isocyanate, halogen, phosphate, phosphonate, phosphonic acid or carboxy, most preferably from phosphonate, phosphonic acid, or a semi-ester thereof), or a salt thereof;
n is an integer from 1-20, preferably from 1-6, such as 1, 2 or 3, e.g., 1; and
X⁻ is a negatively charged counterion;

In certain preferred embodiments, the method comprises reacting a compound of Formula (X) with a compound of Formula (XI)

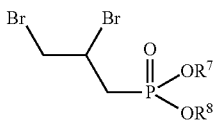

Formula (X)

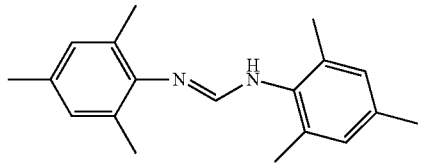

Formula (XI)

in the presence of a base to prepare a compound of Formula (V)

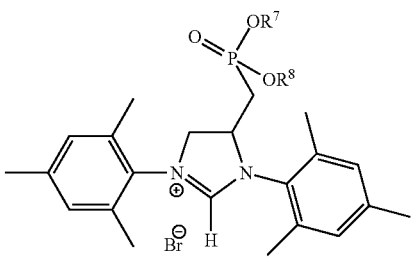

Formula (V)

wherein $R^7$ and $R^8$ are independently H or alkyl or a salt thereof.

In one aspect, the invention provides a method for preparing a transitional metal complex, comprising contacting a transition metal complex with an imidazolinium compound of Formulas (I), (II) or (V), e.g., in the presence of a base.

In certain embodiments, the method comprises reacting a transition metal complex with a compound of Formula (I) to prepare a compound of Formula (III).

In certain embodiments, the method comprises reacting a transition metal complex with a compound of Formula (II) to prepare a compound of Formula (IV)

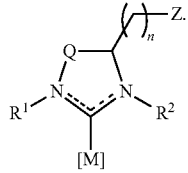

Formula (IV)

In certain preferred embodiments, the method comprises reacting a transition metal complex with a compound of Formula (V) to prepare a compound of Formula (VI)

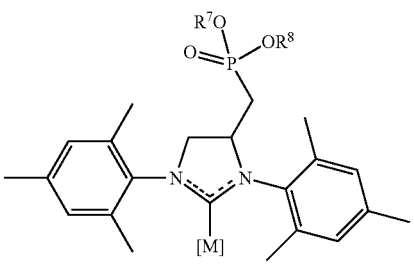

Formula (VI)

wherein $R^7$ and $R^8$ are independently H or alkyl or a salt thereof.

In certain embodiments, the method comprises reacting a compound of Formula (III), (IV) or (VI) with a transition metal complex.

In certain embodiments, the transition metal complex comprises Ti, V, Cr, Mn, Fe, Co, Ni, Cu, Zn, Mo, Ru, Rh, Pd, Ag, Cd, Ta, W, Os, Ir, Pt or Au.

In certain preferred embodiments, the transition metal complex comprises Au, Ag or Ru.

In one aspect, the invention provides a method for preparing a solid-supported catalyst, comprising coupling a compound of Formulas (I)-(VI) to a solid support bearing functional groups that can react with the functional group of the compound.

The invention contemplates the use of any functional group capable of facilitating linkage of the heterocycle to a solid support. In certain embodiments, when linking to the solid support, the functional group of the compound attaching to the solid support will be a leaving group (such as halogen) that is displaced by a nucleophilic group of the solid support. In certain embodiments, when linking to the solid support, the functional group of the compound attaching to the solid support will be transformed into another functional group by reaction with the solid support, e.g., an isocyanate may become a urea or carbamate, an ester may become an amide, and a thiol may become a disulfide. In certain embodiments, when linking to the solid support, the functional group of the compound attaching to the solid support will remain of the same type, e.g., a phosphate, phosphonate, or organosilane may remain a phosphate, phosphonate, or organosilane, albeit with different substituents.

In certain embodiments, the functional group of the compound is organosilane, ester, amino, hydroxyl, isocyanate, halogen, sulfate, sulfonic acid, phosphate, phosphonate, phosphonic acid or carboxy (preferably from organosilane, ester, amino, hydroxyl, isocyanate, halogen, phosphate, phosphonate, phosphonic acid or carboxy, most preferably from phosphonate, phosphonic acid, or a semi-ester thereof), or a salt thereof.

In certain embodiments, the functional group of the compound is ester, amino, hydroxyl, isocyanate, halogen, sulfate, sulfonic acid, phosphate, phosphonate, phosphonic acid or carboxy (preferably from ester, amino, hydroxyl, isocyanate, halogen, phosphate, phosphonate, phosphonic acid or carboxy, most preferably from phosphonate, phosphonic acid, or a semi-ester thereof), or a salt thereof.

In certain preferred embodiments, the functional group of the compound is phosphonate, phosphonic acid or semi-ester thereof, or a salt thereof.

In certain embodiments, the phosphonate, phosphonic acid or semi-ester thereof, or salt thereof, of a compound of Formula (I)-(VI) is tethered to a metal oxide support.

In certain embodiments, the phosphonate, phosphonic acid or semi-ester thereof, or salt thereof, of a compound of Formula (I)-(VI) is tethered to an alumina, silica, titania, zirconia or iron oxide solid support.

In certain embodiments, the method comprises reacting a solid-supported compound of Formula (I), (II) or (V) with a transition metal complex.

In certain embodiments, the method comprises reacting a solid-supported compound of Formula (III), (IV) or (VI) with a transition metal complex.

II. Definitions

The terms "halogen", "halide" and "halo", as used herein, mean halogen and include fluoro, chloro, bromo and iodo.

The terms "hydroxyl" or "hydroxy" refer to the group —OH.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g., methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The terms "amine" and "amino" are art-recognized and refer to both unsubstituted and substituted amines and salts thereof, e.g., a moiety that can be represented by

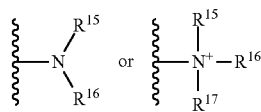

wherein $R^{15}$, $R^{16}$, and $R^{17}$ each independently represent a hydrogen or a hydrocarbyl group, or $R^{15}$ and $R^{16}$ taken together with the N atom to which they are attached complete a heterocycle having from 4 to 8 atoms in the ring structure.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "aralkyl", as used herein, refers to an alkyl group substituted with one or more aryl groups.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "cycloalkylalkyl", as used herein, refers to an alkyl group substituted with one or more cycloalkyl groups.

The term "ester", as used herein, refers to a group —C(O)OR$^{18}$ wherein R$^{18}$ represents a hydrocarbyl group, such as an alkyl group or an aralkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen-containing heteroaryl" refers to heteroaryl wherein any heteroatoms are N. The term "heteroarylene" refers to a divalent heteroaryl.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "organosilane" refers to a moiety containing a silicon atom bonded to at least one alkyl, alkoxy, aryl, heteroaryl, hydroxyl, halogen or amino group. Suitable organosilanes are alkoxysilanes, alkylsilanes, silanols, arylsilanes, halosilanes or amiosilanes.

The terms "transition metal complex" refer to a metallic atom or ion and the surrounding atoms, molecules or ions coordinated to it, known as ligands and complexing agents. Examples of metallic atoms are Ru, Rh, Pd, Pt, Ag, Cd, Mo, Ta, Os, Au, W.

The term "counterion" refers to the ion that accompanies an ionic species to maintain charge neutrality. Examples of negatively charged counterions are $Cl^-$, $Br^-$, $I^-$, $F^-$, $BF_4^-$. Examples of positively charged counterion ions are $H^+$, $Li^+$, $Na^+$, $Mg^{2+}$, $Ca^{2+}$.

The term "mesityl" refers to 1,3,5-trimethylphenyl.

The term "solubilizing group" refers to a moiety that has hydrophilic character sufficient to improve or increase the water-solubility of the compound in which it is included, as compared to an analog compound that does not include the group. Suitable solubilizing groups are carboxylic acids, sulfonic acids, phosphoric acids, phosphonic acids, quarternary ammonium groups, heteratoms, heteroatomic groups.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds.

The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "alkyl" group or moiety implicitly includes both substituted and unsubstituted variants.

At various places in the present specification substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

For a number qualified by the term "about", a variance of 2%, 5%, 10% or even 20% is within the ambit of the qualified number.

III. General Scheme

The general scheme provides an exemplary reaction sequence of the method of the invention, and was described in U.S. Patent Application 61/664,571, which is incorporated herein by reference.

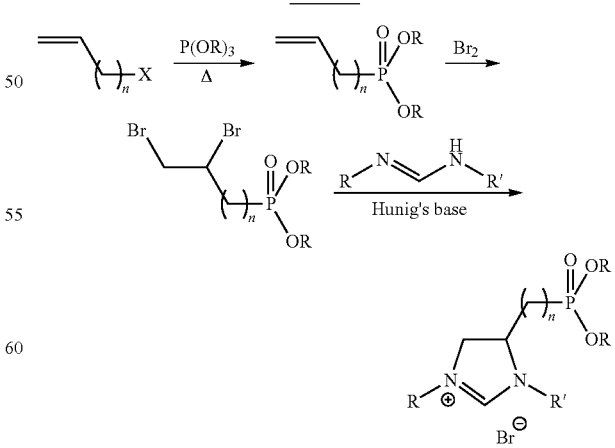

wherein R is H, lower alkyl or unsubstituted or substituted aryl; R' is unsubstituted or substituted aryl; and n is an integer from 1-20, preferably from 1-6, such as 1, 2 or 3.

IV. Preparation

The compounds disclosed herein can be prepared in a variety of ways known to one skilled in the art of organic synthesis, and in analogy with the exemplary compounds whose synthesis is described herein. The starting materials used in preparing these compounds may be commercially available or prepared by known methods. Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

V. Exemplification

The invention now being generally described, it will be more readily understood by reference to the following examples which are included merely for purposes of illustration of certain aspects and embodiments of the present invention, and are not intended to limit the invention.

All reagents and solvents were purchased from commercial vendors and used as received. NMR spectra were recorded on a Varian 300 MHz spectrometer as indicated.

Proton chemical shifts are reported in parts per million (ppm; δ) relative to CDCl$_3$ solvent ($^1$H δ=7.26). NMR data are reported as follows: chemical shifts, multiplicity (obs=obscured, app=apparent, br=broad, s=singlet, d=doublet, t=triplet, q=quartet, m=multiplet); coupling constant(s) in Hz; integration. Unless otherwise indicated, NMR data were collected at 25° C.

The N,N'-bis(mesityl)formamidine was prepared as previously reported, from triethyl orthoformate and 2,4,6-trimethylaniline with acetic acid as a catalyst. [Kuhn et al, *Org. Lett.* 2008, 10, 10, pages-2075-2077] In general, phosphonate substituted alkenes can be prepared from the terminal bromide, through an Arbuzov reaction with triethylphosphite. Allyl diethyl phosphonate, bromine, diisopropylethylamine and ethanol were obtained from Sigma Aldrich and used without further purification.

Diethyl (1,2-dibromopropyl)phosphonate

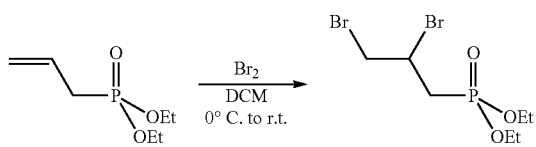

5 grams of diethyl allylphosphonate was dissolved in 100 mL dichloromethane and cooled to 0° C. Bromine (1.1 equivalents) was added over 5 minutes with rapid stirring. The solution was allowed to warm up to room temperature and stirred for 5 hours. Filtration over activated charcoal and concentration provided the product in good yield and purity.

NMR (CDCl$_3$, 300 MHz): $^{31}$P δ=24.570, $^1$H δ=4.43 (m, 1H), 4.24-4.05 (m, 4H), 3.94 (ddd, J=10.8, 4.4, 2.2 Hz, 1H), 3.79 (dd, J=10.8, 7.3 Hz, 1H), 2.79 (ddd, J=18.8, 15.8, 6.1 Hz, 1H), 2.39 (ddd, J=18.5, 15.8, 7.3 Hz, 1H), 1.35 (t, J=7.1 Hz, 6H).

Phosphonate Functionalized Imidazolinium (5-((diethoxyphosphoryl)methyl)-1,3-dimesityl-4,5-dihydro-1H-imidazol-3-ium) bromide

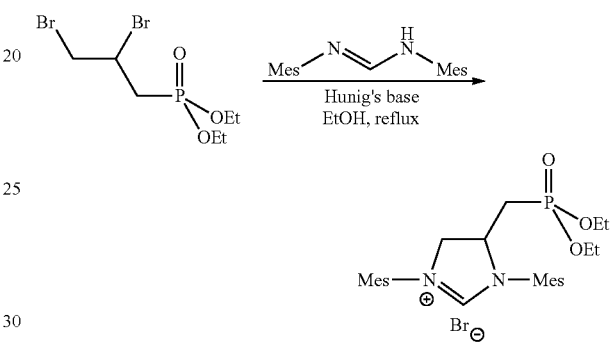

N,N'-bis(mesityl)formamidine (3.03 g), diethyl (1,2-dibromopropyl)phosphonate (4.10 g) and diisopropylethylamine (2.3 mL) were added to a Schlenk-type flask and suspended in ethanol (16 mL). A magnetic stirbar was added; the flask was evacuated until the solution began to bubble and sealed under static vacuum. The reaction was stirred and heated to 120° C. for 4 hours. The reaction mixture was concentrated, dissolved in dichloromethane, washed with water, and concentrated again. The off-white solid was washed with ether and recrystallized from acetone/hexanes, to afford the product as a hygroscopic white solid.

Calculated Mass (M+): 457.2620; Measured Mass: 457.2608; NMR (CDCl$_3$, 300 MHz): $^{31}$P δ=23.290, $^1$H δ=10.57 (s, 1H), 7.05-6.95 (br, 4H), 4.99 (m, 1H), 4.50 (t, J=11.9 Hz, 1H), 4.25 (dd, J=12.5, 9.4 Hz, 1H), 4.18-4.04 (m, 4H), 2.50-2.25 (br, 18H), 2.17 (s, 2H), 1.30 (ddd, J=7.3, 6.8, 1.7 Hz, 6H).

Salt Metathesisc (5-((diethoxyphosphoryl)methyl)-1,3-dimesityl-4,5-dihydro-1H-imidazol-3-ium) tetrafluoroborate

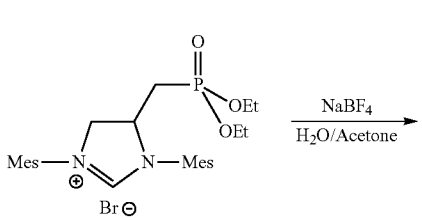

-continued

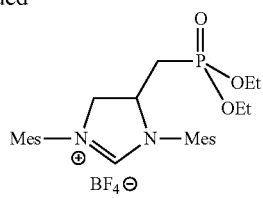

The BF$_4^-$ salt of the phosphonate functionalized imidazolinium compound was prepared by simply adding an aqueous solution of excess NaBF$_4$ to an acetone solution of the imidazolinium. After stirring for 15 minutes, the acetone was removed en vacuo and the compound was extracted in dichloromethane. The organic layer was washed with water, dried with MgSO$_4$ and concentrated to afford the product as a white solid. This salt was significantly less hygroscopic than the bromide salt.

Calculated Mass (M+): 457.2620; Measured Mass: 457.2614; NMR (CDCl$_3$, 300 MHz): $^{31}$P δ=22.979, $^1$H δ=8.49 (br, 1H), 7.05-6.94 (br, 4H), 5.15-4.98 (m, 1H), 4.56 (t, J=12.0 Hz, 1H), 4.28 (dd, J=12.6, 9.8 Hz, 1H), 4.10 (tt, J=7.1, 1.6 Hz, 4H), 2.41-2.29 (br, 18H), 2.27 (br, 2H), 1.30 (td, J=7.1, 2.0 Hz, 6H).

Ag Metallation

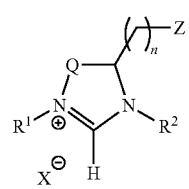

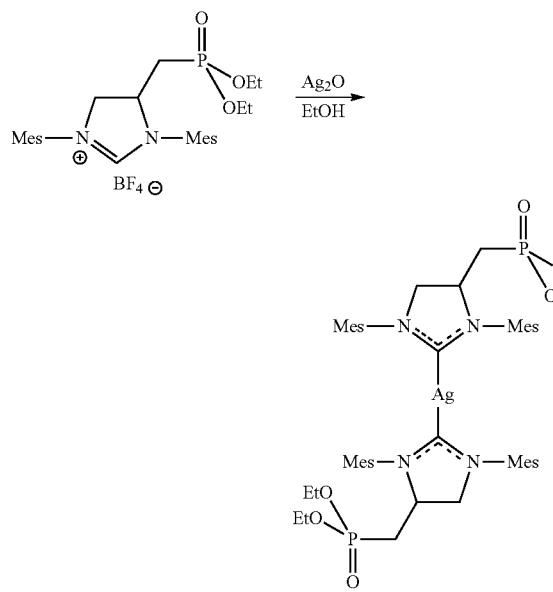

The BF$_4$ salt of the phosphonate functionalized imidizolinium (90 mg) and Ag$_2$O (25 mg) were dissolved in 8 mL EtOH in a scintillation vial, and the headspace of the reaction was purged with Ar. The reaction was stirred at room temperature for 5 hours, then filtered over diatomaceous earth and concentrated to afford the product.

Calculated Mass (M+): 1021.413; Measured Mass: 1021.417; NMR (CD$_2$Cl$_2$, 300 MHz): $^{31}$P δ=24.873, $^1$H δ=7.10-6.80 (br, 8H), 4.50 (br, 1H), 4.14-3.87 (m, 9H), 3.80-3.50 (m, 4H), 2.46-2.19 (br, 17H), 2.01-1.75 (br, 19H), 1.75-1.62 (br, 4H), 1.20 (dtd, J=7.0, 4.5, 2.3 Hz, 12H).

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of Formula (II):

Formula (II)

[Structure]

wherein:
R$^1$ and R$^2$ are independently selected from H, substituted or unsubstituted alkyl, substituted or unsubstituted aryl, and substituted or unsubstituted heteroaryl;
Q is CR$^3$R$^4$;
X$^-$ is a negatively charged counterion;
R$^3$ and R$^4$ are independently selected from H, substituted or unsubstituted alkyl, substituted or unsubstituted aryl, and substituted or unsubstituted heteroaryl;
Z is selected from phosphate, phosphonate, and phosphonic acid, or a semi-ester thereof, or a salt thereof; and
n is an integer from 1-20.

2. The compound according to claim 1, wherein R$^1$ and R$^2$ are independently substituted or unsubstituted aryl.

3. The compound according to claim 1, wherein R$^3$ and R$^4$ are both H.

4. The compound according to claim 1, having the structure of Formula (V):

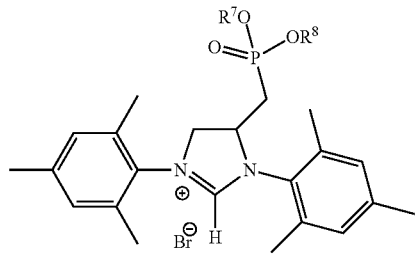

Formula (V)

wherein R$^7$ and R$^8$ are independently H or alkyl, or a salt thereof.

5. A method for preparing a transitional metal complex, comprising contacting a transition metal complex with an imidazolinium compound of claim 1.

6. A method for preparing a solid-supported catalyst, comprising coupling a compound of claim 1 to a solid support bearing functional groups that react with Z.

7. The compound according to claim 1, wherein Z is a phosphonate or a phosphonic acid or semi-ester thereof, or a salt thereof, and Z is tethered to a metal oxide support.

8. The compound according to claim 1, wherein Z is a phosphonate or a phosphonic acid or semi-ester thereof, or a salt thereof, and Z is tethered to alumina, silica, titania, zirconia or iron oxides.

9. The compound according to claim 1, wherein R$^1$ or R$^2$ is selected from substituted alkyl, substituted aryl, and substituted heteroaryl, wherein each substituent is a solubilizing group selected from a carboxylic acid, a sulfonic acid, a phosphoric acid, a phosphonic acid, a quaternary ammonium group, a heteroatom, and a heteroatomic group.

10. The compound according to claim 1, wherein Z is a phosphonate.

11. A compound of Formula (IV):

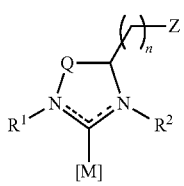

Formula (IV)

wherein:
R$^1$ and R$^2$ are independently selected from H, substituted or unsubstituted alkyl, substituted or unsubstituted aryl, and substituted or unsubstituted heteroaryl;
Q is CR$^3$R$^4$;
R$^3$ and R$^4$ are independently selected from H, substituted or unsubstituted alkyl, substituted or unsubstituted aryl, and substituted or unsubstituted heteroaryl;
Z is selected from phosphate, phosphonate, and phosphonic acid, or a semi-ester thereof, or a salt thereof;
n is an integer from 1-20; and
[M] is a transition metal complex.

12. The compound according to claim 11, having the structure of Formula (VI):

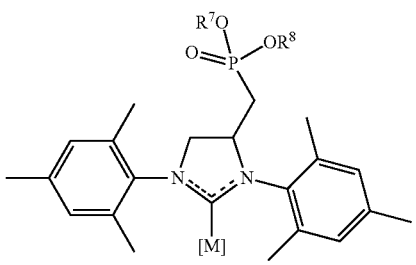

Formula (VI)

wherein R$^7$ and R$^8$ are independently H or alkyl, or a salt thereof.

13. A method for preparing a compound of Formula (II)

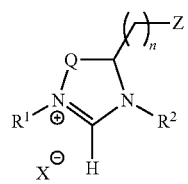

Formula (II)

wherein:
R$^1$ and R$^2$ are independently selected from H, substituted or unsubstituted alkyl, substituted or unsubstituted aryl, and substituted or unsubstituted heteroaryl;
Q is CR$^3$R$^4$;
R$^3$ and R$^4$ are independently selected from H, substituted or unsubstituted alkyl, substituted or unsubstituted aryl, and substituted or unsubstituted heteroaryl;

Z is selected from phosphate, phosphonate, and phosphonic acid, or a semi-ester thereof, or a salt thereof;
n is an integer from 1-20; and
X$^-$ is a negatively charged counterion;
the method comprising reacting a compound of Formula (IX) with the compound of Formula (VIII) in the presence of a base

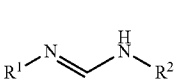

Formula (VIII)

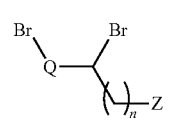

Formula (IX)

to provide the compound of Formula (II).

14. The method according to claim 13, wherein R$^1$ and R$^2$ are independently substituted or unsubstituted aryl.

15. The method according to claim 13, wherein R$^3$ and R$^4$ are both H.

16. The method according to claim 13, wherein the compound has a structure of Formula (V):

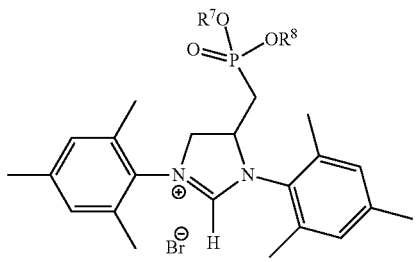

Formula (V)

wherein
R$^7$ and R$^8$ are independently H or alkyl, or a salt thereof; and
the method comprises reacting a compound of Formula (X) with a compound of Formula (XI) in the presence of a base

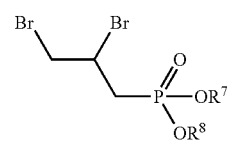

Formula (X)

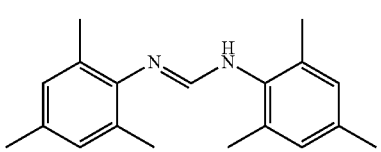

Formula (XI)

to provide the compound of Formula (V), wherein the identities of R$^7$ and R$^8$ may differ between the compound of Formula (X) and the compound of Formula (V).

* * * * *